US008469941B2

United States Patent
Hartlep et al.

(10) Patent No.: US 8,469,941 B2
(45) Date of Patent: Jun. 25, 2013

(54) INTRACRANIAL CATHETER

(75) Inventors: Andreas Hartlep, Weyarn (DE); Christoph Pedain, Munich (DE)

(73) Assignee: Brainlab AG, Feldkirchen (DE)

( * ) Notice: Subject to any disclaimer, the term of this patent is extended or adjusted under 35 U.S.C. 154(b) by 0 days.

(21) Appl. No.: 12/950,223

(22) Filed: Nov. 19, 2010

(65) Prior Publication Data

US 2011/0066133 A1 Mar. 17, 2011

Related U.S. Application Data

(63) Continuation of application No. 11/377,626, filed on Mar. 16, 2006, now abandoned.

(60) Provisional application No. 60/680,129, filed on May 12, 2005.

(30) Foreign Application Priority Data

Mar. 16, 2005 (EP) .................................. 05005724

(51) Int. Cl.
*A61M 31/00* (2006.01)
*A61M 25/00* (2006.01)

(52) U.S. Cl.
USPC ............................. 604/500; 604/264; 604/523

(58) Field of Classification Search
USPC .......................... 604/500, 264, 271, 523, 525
See application file for complete search history.

(56) References Cited

U.S. PATENT DOCUMENTS

| 5,423,774 | A | 6/1995 | Fischell et al. |
| 5,431,637 | A | 7/1995 | Okada et al. |
| 5,891,108 | A | 4/1999 | Leone et al. |
| 6,214,887 | B1 * | 4/2001 | Cote et al. ...................... 514/712 |
| 7,815,623 | B2 | 10/2010 | Bankiewicz et al. |
| 2002/0087143 | A1 * | 7/2002 | Forsberg ....................... 604/523 |
| 2003/0135200 | A1 * | 7/2003 | Byrne ........................... 604/544 |
| 2004/0102697 | A1 * | 5/2004 | Evron ........................... 600/424 |
| 2006/0064011 | A1 * | 3/2006 | Hong ............................. 600/435 |

OTHER PUBLICATIONS

European Search Report corresponding to European Patent Application No. 05 00 5724 dated Sep. 28, 2005.

* cited by examiner

*Primary Examiner* — Bhisma Mehta

(74) *Attorney, Agent, or Firm* — Renner, Otto, Boisselle & Sklar, LLP

(57) ABSTRACT

A catheter having an outer profile which is formed such that a path length along an outer surface of the catheter is greater than the corresponding length of the catheter, and to a method for determining the shape of a catheter, and wherein the elasticity and/or conductivity of the tissue into which the catheter is to be introduced is taken into account in order to determine the outer profile of the catheter.

8 Claims, 3 Drawing Sheets

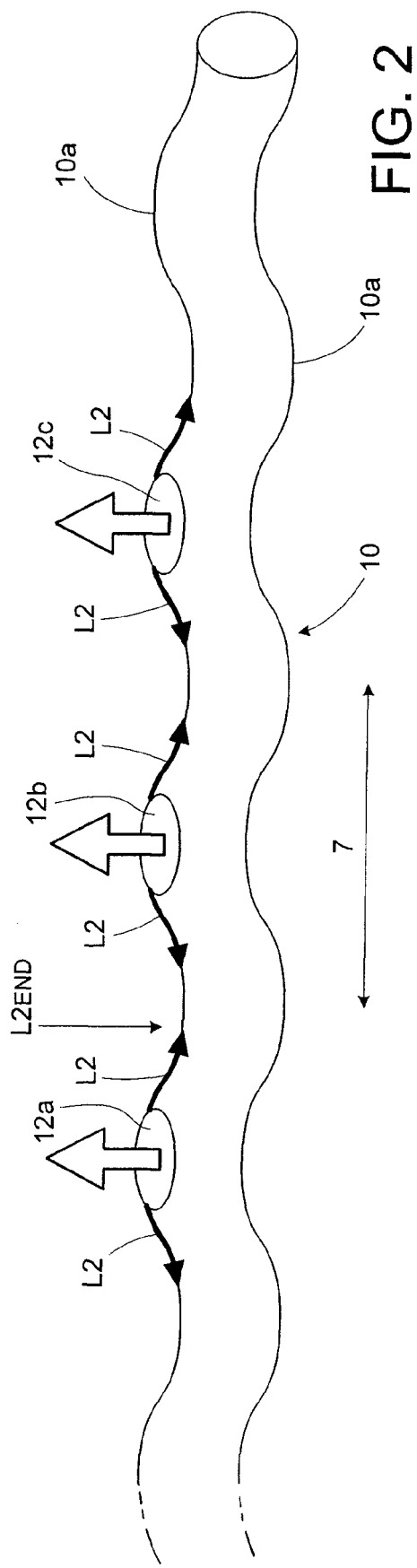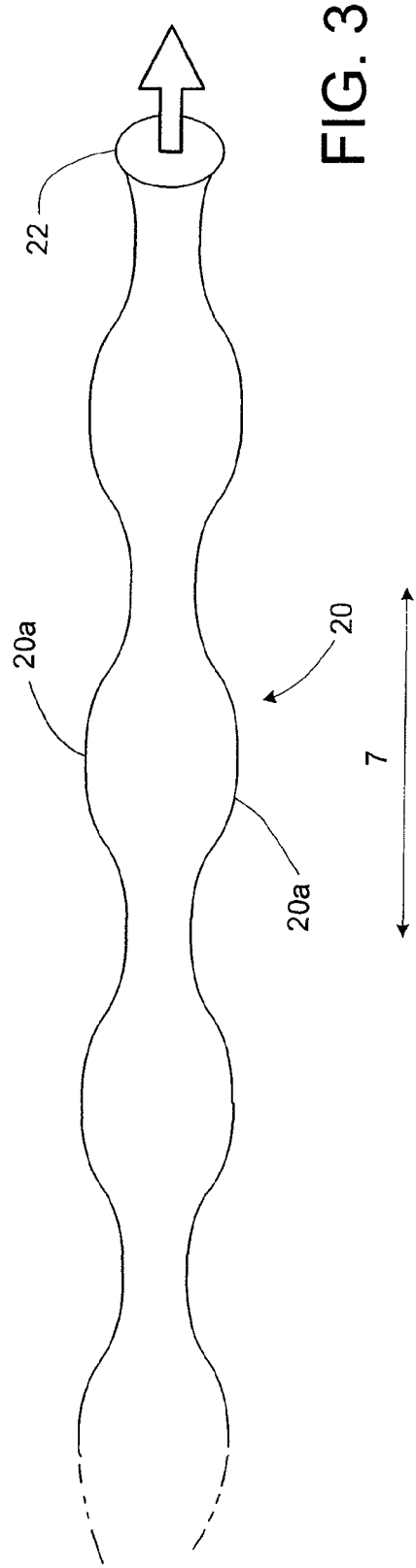

INTRACRANIAL CATHETER

RELATED APPLICATION DATA

This application is a continuation of U.S. application Ser. No. 11/377,626 filed on Mar. 16, 2006, now abandoned which claims priority of U.S. Provisional Application No. 60/680,129 filed on May 12, 2005.

FIELD OF THE INVENTION

The present invention relates to a catheter and, more particularly, to an intracranial catheter that reduces a backflow distance of a liquid dispensed by the catheter.

BACKGROUND OF THE INVENTION

Various catheters are known that differ with regard to their shape and size. For example, catheters can exhibit various diameters and lengths. Further, an opening for dispensing a liquid can be located at a distal end of the catheter or along the catheter.

For directly treating a diseased area of the body such as, for example, brain tumors or neurodegenerative diseases, it is advantageous if medicines or therapeutic agents can be directly supplied to the diseased area in the body. In order to supply a medicine to a diseased tissue, a catheter is introduced into the body, such that a catheter opening is in or near the diseased tissue or area to be treated.

However, using paediatric ventricle catheters such as hitherto have been used for treating such diseased tissue, it is not possible to dispense a particular amount of a substance safely and/or reliably in a desired area of a body. This is due in part to liquid (e.g., the substance) exiting the catheter opening and initially flowing substantially back along the surface portion of the catheter that has penetrated the tissue matrix. Thus, the liquid flows back along the catheter trajectory, away from the area to be treated. This reverse flow phenomenon is called "backflow", wherein a reverse flow length L is proportional to the fifth root of $Q \times r^4$, where Q is the flow rate of the substance exiting the catheter and r is the outer radius of the catheter. If a sufficient supply of a substance to be administered is to be ensured, this reverse flow or backflow length L limits the ways and/or restricts the locations at which a catheter can be used or inserted. If, for example, an intracranial surface such as a sulcus is penetrated by the catheter used for an infusion or injection, it is highly probable that the back flowing fluid will disperse along the surface of the sulcus and will not reach the desired target (e.g., in front of the catheter tip). A substance exiting an opening of the catheter will only flow into the intercellular space of the tissue to be treated once the pressure exerted by the tissue on the ascending liquid adjacent to the outer side of the catheter is greater than the pressure or resistance of the intercellular space of the tissue in front of the exit opening of the catheter.

SUMMARY OF THE INVENTION

The present invention provides a catheter wherein an outer profile is formed such that a path length in the longitudinal direction or supply direction of the catheter along at least a portion or section of an outer surface of the catheter (e.g., the length of a reverse flow path of a substance exiting a front or lateral opening of the catheter) is greater than a corresponding length of the catheter (e.g., the penetration length of the catheter or length in which the catheter can penetrate into tissue). Accordingly, a relatively long path length along an outer side of the catheter is provided, when compared to the longitudinal length or penetration depth of the catheter. The relatively long path length or distance enables the pressure created by the tissue on the liquid to be established in a relatively short distance from the catheter opening and, therefore, a relatively large portion of the substance to be dispensed can be supplied to an area in front of or near the catheter opening or openings. The outer surface or outer profile of the catheter preferably is shaped such that for a given region extending along the longitudinal extent of the catheter, the length along an outer surface area of the catheter is greater than the longitudinal length of said given region. Preferably, the outer wall of the catheter undulates along the length of the catheter, such as in a snake-like fashion or with alternating bulges and valleys, or a combination thereof.

By increasing the reverse flow path along an outer surface of the catheter, an increased reverse flow length is exhibited for a given penetration depth (as compared for instance to a tubular or cylindrical catheter) along every possible reverse flow path or along a portion of the possible reverse flow paths. Thus, it is possible to improve the supply of substance or fluid to tissue (e.g., to the white matter of the brain). Further, the precision at which the substance may be delivered to the brain can be increased since the delivery will be more localized. This enhances the predictability of the fluid dispersion in the tissue and, thus, enables simulations to be performed with increased precision. As the fluid or substance dispersion is improved, the catheter may be used in a more reliable and efficient manner. For example, the location and/or parameters for dispensing a liquid (e.g., pressure or flow rate) can be planned with greater precision, which can improve the success of the treatment.

The catheter may be formed such that the outer surface, profile or shape of the catheter (e.g., an elongated portion of the catheter) varies periodically and/or in sections in the longitudinal direction of the catheter (e.g., from a proximal end to a distal end, or merely across a section of the catheter). The outer wall of the catheter may be undulating, for example, with the catheter having a substantially constant cross-section, the center of which defines an undulating path along the longitudinal direction of the catheter. The undulations can be formed as a plurality of contiguous undulations spaced apart less than a length of one undulation, each having a rounded crest and valley, and a depth of each valley can be less than a radius of the elongated portion at an adjacent crest. Alternatively or additionally, the catheter may be formed such that the cross-section or outer diameter of the catheter varies along the length of the catheter, wherein the catheter can exhibit an undulating shape that includes sections having smaller and greater outer diameters. Again, the undulations can be formed as a plurality of contiguous undulations spaced apart less than a length of one undulation, each having a rounded crest and valley as noted above. The elongated portion, when inserted into tissue, minimizes backflow of the administered fluid substance along the outer surface of the catheter.

The catheter may include one or more openings that can be provided at the front end or distal end and/or the side of the catheter, for example, and the openings may be formed in the catheter at a crest or valley. The catheter may be formed from a porous or permeable material with or without catheter openings, such that a substance introduced into the catheter can exit the catheter by diffusion.

In a method for determining the shape of a catheter, in particular for determining the outer profile of the catheter, the reverse flow path along the outer side of the catheter can be optimized and maximized. An exemplary reverse flow path along the outer side of the catheter can be seen in FIG. 4, wherein an amplitude and/or undulation length of the reverse flow path of a substance along the surface of the catheter is shown in cross section in the longitudinal direction of the catheter.

When determining an outer shape and/or length of a catheter, the tissue elasticity may be taken into account, such that the contact area between the surface of the catheter and the penetrated tissue may be optimized and maximized, so as to form a small reverse flow channel or not to form a reverse flow channel for the substance to be administered. The contact area between the surface of the catheter and the tissue (the tissue conforming to a contour of the outer surface of the catheter as the catheter is inserted into the tissue so as to define a reverse flow path along the outer surface in which fluid may flow) can determine the reverse flow distance, such that the actual reverse flow distance in the tissue can be shortened, since the surface runs in curves and bends and is not linear or parallel to the longitudinal axis of the catheter. Equally, the conductivity and/or infusion parameters, such as the flow rate or an infusion pressure, for example, may be taken into account when selecting the shape of the catheter.

In accordance with the present invention there is provided a method for minimizing backflow of a substance administered by a catheter along at least a portion of an outer surface of the catheter, the catheter including an elongated portion and at least one front or lateral opening for administering the substance. At least the portion of the catheter is inserted into tissue of a patient, wherein a flow path between the outer surface of the inserted portion of the catheter and the tissue surrounding the inserted portion of the catheter is greater in length than a corresponding length of the inserted portion of the catheter.

According to one aspect of the invention, the method further includes using a catheter having a plurality of undulations along the outer surface of the catheter.

According to one aspect of the invention, using a catheter having a plurality of undulations includes using a catheter having a plurality of contiguous undulations.

According to one aspect of the invention, using a catheter having a plurality of contiguous undulations includes using a catheter having undulations spaced apart less than a length of one undulation.

According to one aspect of the invention, using a catheter having a plurality of contiguous undulations includes using undulations each having a rounded crest and valley, and a depth of each valley is less than a diameter of an adjacent crest.

According to one aspect of the invention, the method includes using a catheter having a cross-section along the plurality of undulations that remains constant in the longitudinal direction.

According to one aspect of the invention, the method includes using a catheter having a cross-section along the plurality of undulations that varies in the longitudinal direction.

The forgoing and other features and embodiments of the invention are hereinafter discussed with reference to the drawings.

BRIEF DESCRIPTION OF THE DRAWINGS

In the annexed drawings:

FIG. 2 illustrates another exemplary undulating catheter having a lateral catheter openings in accordance with the invention;

FIG. 3 illustrates another exemplary undulating catheter having a varying cross-section in accordance with the invention.

DETAILED DESCRIPTION

Figure 1B:
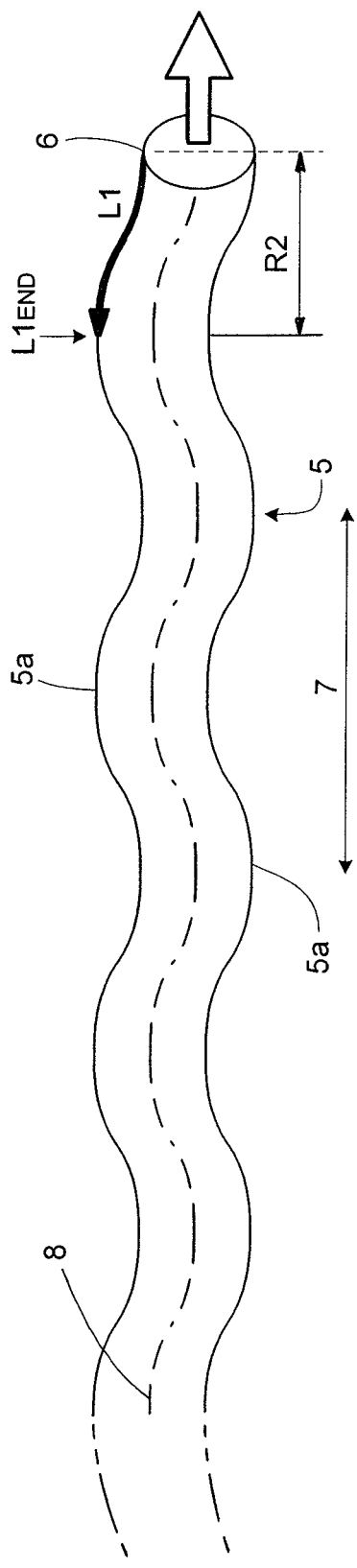
FIG. 1B illustrates an exemplary undulating catheter having a distal catheter opening in accordance with the invention.
Figure 1A:
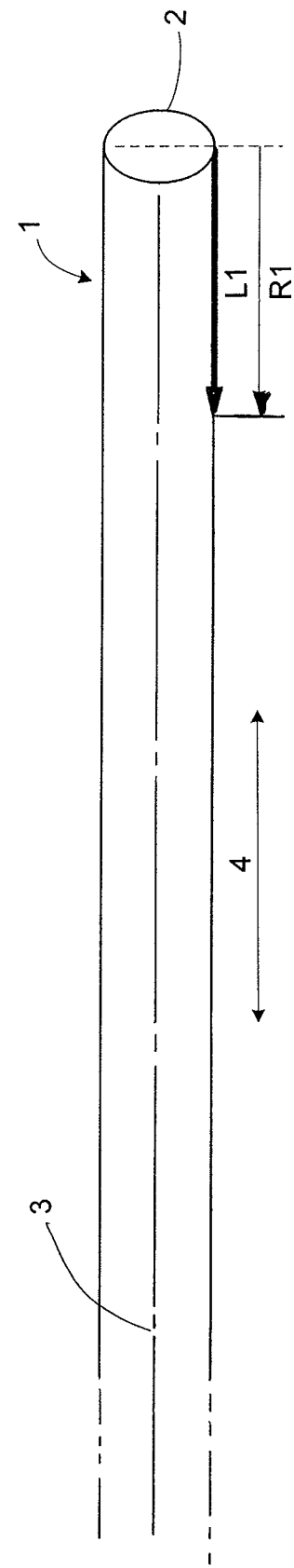
FIG. 1A illustrates a conventional catheter.

FIG. 1A shows a conventional catheter 1 and more particularly a dispensing portion thereof that is inserted into a body or tissue and which is provided with an opening through which an agent can be administered to the body or tissue, such as the opening 2 at the end of the catheter. The catheter is of uniform cross-section and has a center axis 3 extending parallel to the longitudinal direction of the catheter, such longitudinal (penetration) direction being indicated by the arrow 4.

In use, the dispensing portion of the catheter will be inserted into a body or tissue to administer a substance to a target area. The catheter opening 2 preferably is positioned relative to the target area such the substance will be delivered to the target area and the smallest amount possible to the area surrounding the target area. As above discussed, some of the substance exiting the opening will backflow along the outer surface of the catheter and away from the area to be treated. The extent of this backflow is indicated by the length L1 which in the case of a conventional catheter will be equal the longitudinal length R1 of a corresponding region of the catheter.

FIG. 1B shows an exemplary catheter 5 according to the present invention and more particularly a dispensing portion thereof that is inserted into a body or tissue and which is provided with an opening through which an agent can be administered to the body or tissue, such as the opening 6 at the end of the catheter. As shown, the catheter 5 has a cross-section that is approximately constant along the length direction 7 of the catheter dispensing portion, like the prior art catheter of FIG. 1A. The catheter 5, however, has an undulating shape where a central line or axis 8 of the catheter undulates along the longitudinal direction 7 up to the opening 6 at the end of the catheter.

Like the prior art catheter of FIG. 1A, the dispensing portion of the catheter 5 will be inserted into a body or tissue to administer a substance to a target area. The catheter opening 6 preferably is positioned relative to the target area such the substance will be delivered to the target area and the smallest amount possible to the area surrounding the target area. As above discussed, some of the substance exiting the opening will backflow along the outer surface of the catheter and away from the area to be treated. The extent of this backflow is again indicated by the length L1 which length would be the same length of the backflow if the prior art catheter 1 were used given all other conditions being the same. Unlike the case of a conventional catheter, the longitudinal extent R2 of the backflow along the length direction 7 of the catheter will be less than the longitudinal extent R1 of the backflow associated with the prior art catheter, this being the result of the undulating outer surface 5a of the catheter. Consequently, the backflow will extend from the opening 6 by an amount less than what occurs if a prior art catheter is used by the difference between R1 and R2.

As used herein, a longitudinal length is a length measured along the longitudinal extent of the catheter. A longitudinal surface length is a length measured along the outer surface of the catheter in the longitudinal direction. The center line or axial length is a length measured along the center axis of the catheter. Accordingly, in the prior art catheter the longitudinal surface length and axial length will be equal to the longitudinal length of the catheter for a given longitudinal length of the catheter. In the catheter of FIG. 1B, the longitudinal surface length will be greater than the longitudinal length for a given longitudinal length of the catheter and this would also be true of the axial length of the catheter (i.e, the length of the catheter measured along the catheter center line) given that the catheter center line undulates like the outer surface.

FIG. 2 shows another exemplary catheter 10 that includes lateral openings 12a, 12b and 12c for dispensing a substance supplied through the catheter 10, wherein the substance exiting the openings 12a, 12b and 12c only flows a distance L2 from the respective openings. Like the catheter 5 of FIG. 1B, the catheter 10 has an undulating shape or form that increases the length of the outer surface 10a, such that the an end location $L2_{end}$ of the fluid flow remains closer to the respective openings 12a, 12b and 12c than would be achieved using a conventional catheter. In other words, the flow length of the substance exiting each opening will be longer than the longitudinal extent of such flow.

FIG. 3 shows another exemplary catheter 20 with a distal lateral opening 22. The catheter 20 has an undulating form or shape on a surface 20a such as the catheters 5 and 10 of FIGS. 1B and 2. Unlike the catheters 5 and 10, however, the cross-section of the catheter 20 varies in the longitudinal direction 7 to form bulge and valley regions along the length of the catheter.

Figure 4:
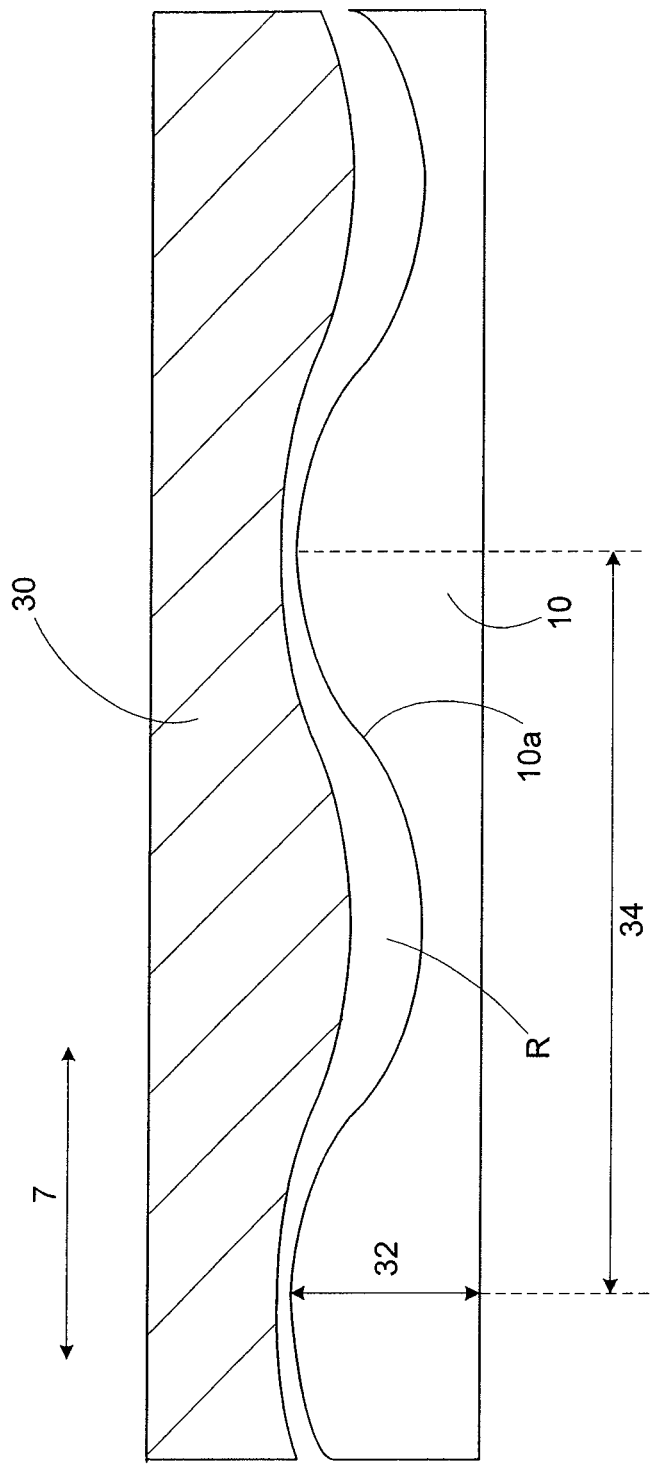
FIG. 4 is a schematic diagram illustrating the functionality or shaping of an exemplary catheter in accordance with the invention.

FIG. 4 shows a schematic diagram of a catheter 10, for example, inserted along an injection channel or trajectory into the tissue 30, wherein the catheter abuts the penetrated tissue 30 via its undulating outer side 10a. Openings for dispensing a substance may be located in the peaks or valleys of the catheter. A reverse flow channel R is formed between the catheter 10 and the tissue 30, wherein the outer profile and/or the material of the catheter 10 is selected such that by taking into account the elasticity of the respective tissue 30, the contact area between the outer surface 10a of the catheter 10 and the tissue 30 is maximized, thereby minimizing the reverse flow channel R. Further, it is advantageous to select the amplitude 32 of the undulating outer shape of the catheter 10 to be greater, the greater the elasticity of the tissue 30 (e.g., amplitude of the undulating shape is proportional to the elasticity of the tissue). Also, it is preferable that the undulation length or pitch (period) 34 of the outer surface 10a of the catheter 10 be reduced if the elasticity of the tissue 30 is high.

outer shape=(elasticity*C1)*sin(elasticity*C2)     Eq. 1

Equation 1 illustrates an exemplary relationship between the catheter shape and elasticity of the tissue, wherein "outer shape" is the outer shape of the catheter, "elasticity" is the elasticity of the tissue, and C1 and C2 are constants. C1 and C2 can range between about 0 and 1, preferably between 0.2 and 0.8, and more preferably between about 0.4 and 0.6.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for minimizing backflow of a fluid substance administered by a catheter along at least a portion of an outer surface of the catheter, said catheter including an elongated portion having a plurality of undulations and at least one front or lateral opening for administering the fluid substance, the method comprising:
    inserting at least the elongated portion of the catheter into tissue of a patient, the tissue conforming to a contour of the outer surface of the catheter to define a reverse flow path along the outer surface in which the fluid substance may flow, wherein the reverse flow path between the outer surface of the inserted portion of the catheter and the tissue surrounding the inserted portion of the catheter is greater in length than a corresponding length of the inserted portion of the catheter; and
    administering the fluid substance through the catheter and into intercellular tissue space, wherein the elongated portion minimizes backflow of the administered fluid substance along the outer surface of the catheter.

2. The method according to claim 1, wherein inserting at least the elongated portion of the catheter having the plurality of undulations includes using a catheter having a plurality of undulations along the outer surface of the elongated portion.

3. The method according to claim 2, wherein using a catheter having a plurality of undulations along the outer surface of the elongated portion includes using a catheter having a plurality of contiguous undulations along the outer surface of the elongated portion.

4. The method according to claim 3, wherein using a catheter having a plurality of contiguous undulations along the outer surface of the elongated portion includes using a catheter having undulations spaced apart less than a length of one undulation.

5. The method according to claim 3, wherein using a catheter having a plurality of contiguous undulations along the outer surface of the elongated portion includes using a catheter having a plurality of contiguous undulations, each undulation having a rounded crest and valley, and a depth of each valley is less than a radius of an adjacent crest.

6. The method according to claim 2, wherein using a catheter having a plurality of undulations along the outer surface of the elongated portion includes using a catheter having a cross-section along the plurality of undulations that remains constant in the longitudinal direction.

7. The method according to claim 2, wherein using a catheter having a plurality of undulations along the outer surface of the elongated portion includes using a catheter having a cross-section along the plurality of undulations that varies in the longitudinal direction.

8. The method according to claim 2, wherein using a catheter having a plurality of undulations along the outer surface of the elongated portion includes using a catheter having the outer surface contour corresponding to the product of elasticity*C1*sin(elasticity*C2), wherein C1 and C2 are constants and elasticity is the tissue elasticity.

* * * * *